(12) United States Patent
Florio et al.

(10) Patent No.: US 6,259,948 B1
(45) Date of Patent: *Jul. 10, 2001

(54) MEDICAL DEVICE

(75) Inventors: Joseph J. Florio, La Canada; Paul A. Levine, Newhall; Mark R. Myers, La Canada, all of CA (US)

(73) Assignee: Pacesetter, Inc., Sylmar, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/191,166

(22) Filed: Nov. 13, 1998

(51) Int. Cl.[7] .................................................. A61N 1/36

(52) U.S. Cl. ................................. 607/9; 607/17

(58) Field of Search .................... 607/9, 17, 18, 607/19

(56) References Cited

U.S. PATENT DOCUMENTS

| | | | |
|---|---|---|---|
| 5,342,404 | * 8/1994 | Alt et al. | 607/19 |
| 5,417,714 | 5/1995 | Levine et al. | 607/9 |
| 5,464,434 | 11/1995 | Alt | 607/6 |
| 5,472,453 | * 12/1995 | Alt | 607/19 |
| 5,476,483 | * 12/1995 | Bornzin et al. | 607/17 |
| 5,501,701 | 3/1996 | Markowitz et al. | 607/9 |
| 5,514,162 | 5/1996 | Bornzin et al. | 607/19 |
| 5,593,431 | 1/1997 | Sheldon | 607/19 |
| 5,676,483 | 10/1997 | Koubek | 403/109 |
| 5,891,176 | * 4/1999 | Bornzin | 607/18 |

OTHER PUBLICATIONS

P.A. Levine, M.D. "New Algorithms: Automatic Mode Switching Neurocardiogenic, Syncope, Sleep Mode, AV/PV Hysteresis, Autocapture, and Others," pp. 1–12, Pacesetter, Inc., a St. Jude Medical Company, (Mar. 1997).*

A. Fitzpatrick, et al "Recurrent Symptoms after Ventricular Pacing In Unexplained Syncope," pp. 619–624, PACE, vol. 13 (5/1990).*

A. Fitzpatrick, et al "Dual–Chamber Pacing Aborts Vasovagal Syncope Induced by Head–Up 60 Degree Tilt," pp. 13–19,PACE, vol. 14(1/1991).*

D. Samoil, et al "Comparision of Single and Dual Chamber Pacing Techniques in Prevention of Upright Tilt Induced Vasovagal Syncope," pp. 36–41, EUR.J.C.P.E., vol. 3, No. 1 (1993).*

S.S. Jasbir, M.D., et al. "Comparision of Cardiac Pacing with Drug Therapy in the Treatment of Neurocardiogenic (Vasovagal) Syncope with Bradycardia or Asystole," pp. 1085–1090, The New England Journal of Medicine, vol. 328 (4/1993).*

W.N. Kapoor, et al "Upright tilt Testing in Evaluating Syncope: A Comprehensive Literature Review," pp. 78–88, The American Journal of Medical, vol. 97 (7/1994).*

S. Oswald, et al. "Asystole after Exercise in Healthy Persons," pp. 1008–1011, Annals of Internal Medicine, vol. 120, No. 12(6/1994).*

M.E.V. Peterson, et al. "Permanent Pacing for Cardioinhibitory Malignant Vasovagal Syndrome, " pp. 274–281, British Heart Journal, vol. 71 (1994).*

D.G. Benditt, M.D., et al. "Cardiac Pacing for Prevention of Recurrent Vasovagal Syncope," pp. 204–209, Annals of Internal Medicine, vol. 123, No. 3 (2/1/1995).*

M.D. Gammage,et al "Intial Experience with a Rate Drop Algorithm in Malignant Vasovagal Syndrome," pp. 45–48, EUR.J.C.P.E., vol. 5, No. 1 (1995).*

\* cited by examiner

*Primary Examiner*—Scott M. Getzow

(57) ABSTRACT

A device in the form of a cardiac pacemaker for treating a malfunctioning heart, in which the intrinsic heart rate information is combined with secondary sensor variance information to select an appropriate therapy for the patient. The cardiac pacemaker has operational capability in the sleep mode and includes a hysteresis function. The hysteresis function is disabled during operation in the sleep mode and a pacing therapy is selected based upon the intrinsic heart rate and sleep mode operation.

13 Claims, 4 Drawing Sheets

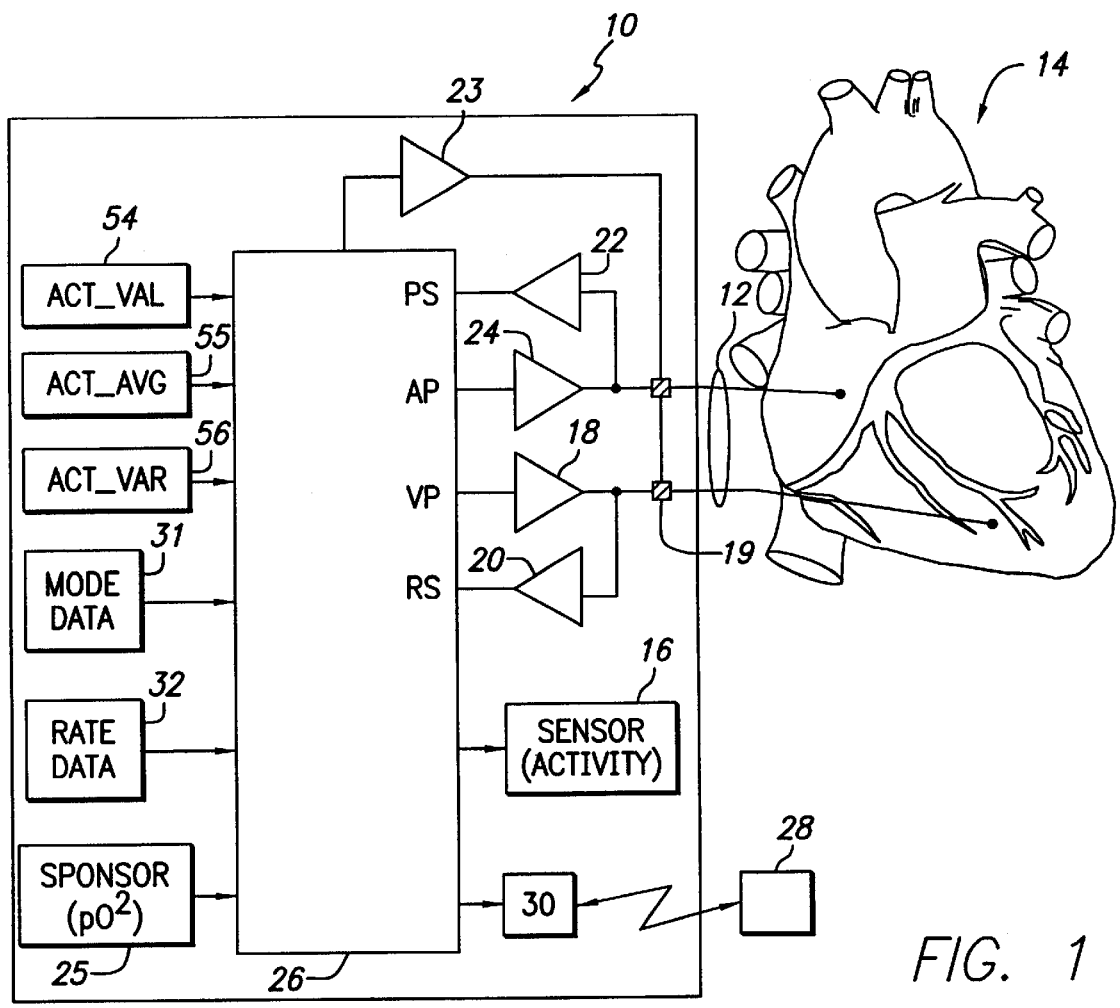
FIG. 1
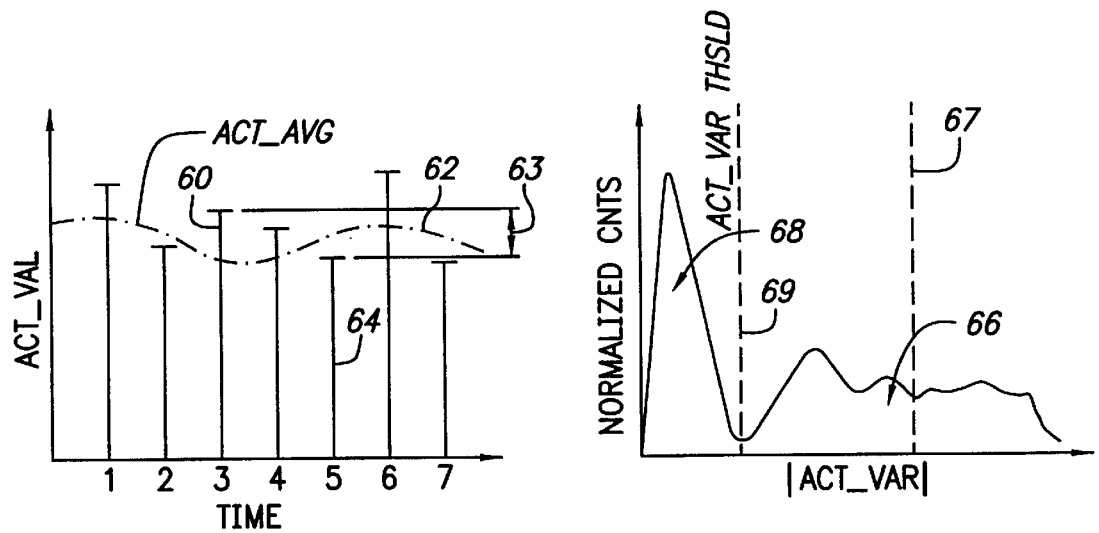
FIG. 2
FIG. 3

MEDICAL DEVICE

FIELD OF THE INVENTION

The invention relates generally to implantable medical devices for managing cardiac rhythm. More particularly the invention relates to a device which alters its operation based upon measured sensor variance. The invention is illustrated in the context of a pacemaker for treating episodes of vasovagal syncope.

BACKGROUND OF THE INVENTION

A prolonged period of asystole is an unambiguous indication for pacing. The more complex issue is what pacing rate is appropriate for the heart and when and under what circumstances should the pacing therapy stop. The traditional demand pacemaker sensed R-wave intervals on a beat-to-beat basis and paced only when the underlying rhythm was below a so called escape interval. Modern therapies for bradycardia are much more complex. Many modern pacemakers have sensors. These sensors provide more information about the cardiovascular state of the patient and efforts are being made to use this additional information to improve the efficacy of pacing therapy. These improvements also expand the indications for pacing. At present, pacing therapies have been proposed for treating vasovagal syncope.

Vasovagal syncope, also called neurally-mediated or neurocardiogenic syncope, is a relatively common entity. It also goes by the name "common faint." For most individuals who are subject to this entity, it occurs very infrequently and can be managed by sitting or lying down when warning symptoms, such as lightheadedness, sweating and nausea, occur. When individuals experience repeated episodes without the usual warning signs, then pharmacologic or pacing therapy is required.

The common "faint" is an example of an interaction between the automatic nervous system and the cardiovascular system. There are several types of faints of which vasovagal syncope is one. Within vasovagal syncope, there are subsets which differ in detail. The typical episode involves a concurrent and precipitous drop in both blood pressure and heart rate. For an ambulatory subject, the resultant sudden loss of cardiac output can result in a potentially injurious fall.

Drugs have been considered the first line of therapy for many of these patients. However the chronic use of drugs for rare episodes of vasovagal syncope is problematic. More recently pacing therapies have been proposed for these patients. For example DDI pacing with hysteresis has been explored as a therapy for this patient group. With DDI hysteresis pacing, a patient with normal sinus function can remain in sinus rhythm most of the time. Vasovagal events which trigger the hysteresis escape interval result in pacing at a relatively high rate to compensate for both asystole and vasodilatation.

It is also possible to trigger a pacing therapy based upon a disease specific rate drop algorithm. See for example U.S. Pat. No. 5,501,701 to Shelton et al. and U.S. Pat. No. 5,501,701 to Markowitz et al. As taught by the patents, a drop in heart rate over a relatively short interval invokes pacing at a programmed higher pacing rate. However, the conventional rate drop algorithm requires several beats before the pacemaker intervenes which is undesirable for a presyncopal patient. Both conventional DDI with hysterisis pacing and the rate drop algorithm are unable to reliably distinguish pathologic from physiologic rate drops. Therefore, the prior pacemakers may pace inappropriately under some circumstances which is undesirable.

SUMMARY OF THE INVENTION

In the present invention certain sensor variance data is used to guide therapy and to alter the behavior of the device to treat vasovagal syncope. This is one example of a broader invention which uses sensor variance data from one or more sensors to control the device. The illustrative pacemaker of this invention uses both measured heart rate and an independent physiologic sensor operating together to determine the occurrence of vasovagal syncope. If an episode of a treatable syncope is detected, the pacemaker quickly elevates the pacing rate to support the patient during the episode.

In operation, the device immediately intervenes to pace the heart at a selected rate if the patient exhibits asystole while the patient's physical activity index indicates a normal physical activity state. This response provides sufficient cardiac output to interrupt the episode. In this illustrative embodiment, two criteria must be met before the therapy is invoked. The first criteria is a characteristic low heart rate derived from the pacemakers sense amplifier and escape interval timer structures. The second criteria is normal patient activity derived from a complimentary physiologic sensor such as physical activity.

The illustrative pacemaker monitors the intrinsic heart rate with the escape interval timer and sense amplifier. The device monitors the metabolic state of the patient by measuring the variance of the patient's activity level. If the pacemaker "escapes" and generates a pace event, then the patient is experiencing asystole which is one example of a sufficiently low heart rate. Next, the pacemaker interrogates the sensor variance. If the sensor variance measurement indicates a normally active patient, then the pacemaker intervenes at a selected rate to treat the declared vasovagal event. In the preferred method, the pacemaker tests the patient activity state after the escape interval times out. However, this desirable sequence is not critical. The principle advantage of the use of the sense amplifier and escape interval timer as one element of the method is that these structures measure the adequacy of the heart rate on a beat-to-beat basis. The principle advantage of the use of sensor variance as an indicator of metabolic state is the high specificity of the measure in distinguishing slowly varying low activity periods like sleep from other more ambiguous metabolic states. Together sensor variance and sensed heart rate permit a rapid accommodation of a "fainting" spell.

Although measured intrinsic heart rate and patient activity variance are used to illustrate this invention, other complementary sensor pairings are contemplated within the scope of the invention as well.

Exemplary pairings include sensors for patient position combined with heart rate and blood pressure combined with heart rate. It should also be understood that the method can be extended to more than one sensor and the method can be used to alter other therapeutic aspects of the device to treat other disorders. It should also be noted that sensor variance can alter other therapy or device parameters. The examples of rate selection and A-V delay interval should not be regarded as limiting.

BRIEF DESCRIPTION OF THE DRAWINGS

Throughout the figures identical reference numerals indicate equivalent structure, wherein:

FIG. 1 is a diagram, showing a pacemaker coupled to a patient's heart;

FIG. 2 is a diagram showing representative data collected in the sensor channel;

FIG. 3 is a diagram showing representative data collected in the sensor channel;

DESCRIPTION OF THE ILLUSTRATIVE EMBODIMENTS

Overview

For purposes of illustration the invention as shown in FIG. 1, is incorporated into a dual-chamber pacemaker 10 with an activity sensor 16 as the independent indicator of the metabolic state of the patient. The pacemaker shown in FIG. 4 operates in the DDI(R) mode while the pacemaker shown in FIG. 5 operates in the DDD mode.

A DDI(R) mode pacemaker does not track the patient's atrial rhythm which is appropriate for vasovagal patients that have normal sinus node function. In this embodiment, the device alters the pacing rate when the measured sensor variance meets certain criteria. The illustrative DDI(R) pacemaker of FIG. 4 has an activity modulated escape interval and it monitors the "variance" of activity to determine the activity state of the patient. These aspects of the invention and illustrative implementations are described in more detail in U.S. Pat. No. 5,676,483 to Bornzin et al.; U.S. Pat. No. 5,417,714 to Levine et al.; and U.S. Pat. No. 5,514,162 to Bornzin et al. each of these patents is owned by the assignee of the present invention and these patents are incorporated by reference herein in their entirety.

Figure 5:
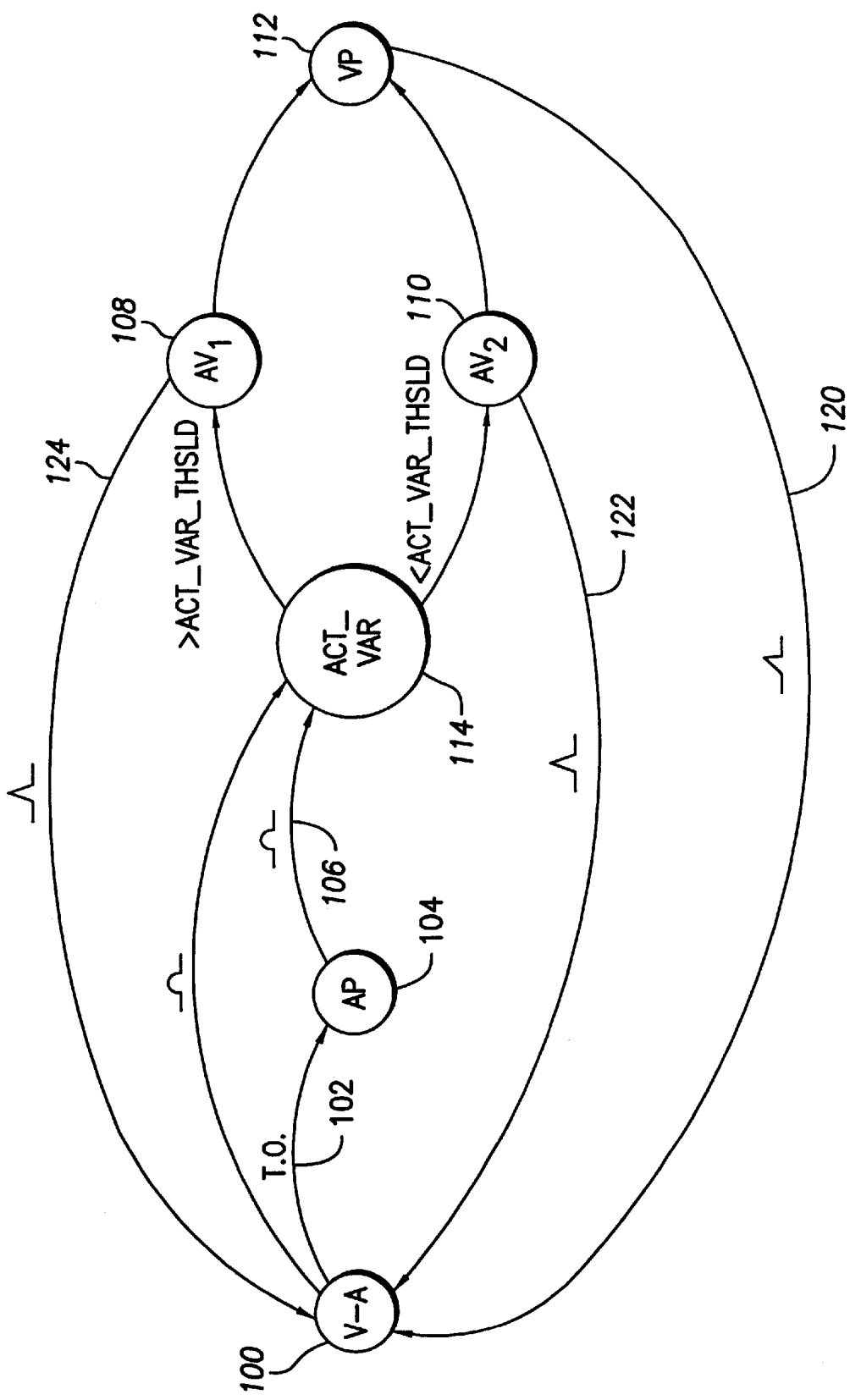
FIG. 5 is a state diagram of a dual-chamber pacemaker incorporating the invention.

A DDD mode pacemaker is shown in FIG. 5. This embodiment illustrates how the sensor variance can be used to altering another parameter of the therapy. In the exemplary pacemaker, the device alters the AV delay of the pacemaker.

Both DDI(R) and DDD pacing modalities are desirable because the maintenance of atrio-ventricular synchrony maximizes ventricular filling providing a high stroke volume which is particularly helpful to a hypotensive patient.

As discussed below other therapy choices and sensor systems are within the scope of the disclosure.

Detailed Description

FIG. 1 is a schematic block diagram which shows the pacemaker 10 connected to an implanted lead system 12 which is coupled to the patient's heart 14. The pacemaker 10 has a ventricular channel which includes a ventricular sense amplifier 20 (RS) and a ventricular pulse generator 18 (VP). The pacemaker also includes an atrial channel which includes an atrial sense amplifier 22 (PS) and an atrial pulse generator 24 (AP). The atrial and ventricular channels generate sense event signals in response to detected depolarization of the patient's heart and stimulate the heart in response to pace event signals. The atrial and ventricular channels are coupled to pacing logic means 26 which may take the form of a microprocessor operating under the control of a stored program or a hardwired state machine. The particular logic means illustrated in the figures is a processor also labeled 26. A remote programmer 28 is provided to the attending physician to permit "programming" of the operating modality of the pacemaker 10 and certain other therapy parameters through a bidirectional transceiver 30 coupled to the pacemaker processor 26. The pacemaker processor 26 may operate in any of the known ICHD pacing modes. DDI(R) and DDD are specifically illustrated in the figures. The principle activity of the logic means 26 is to track various escape interval times and to compute certain sensor measurements which influence pacemaker operation. In operation, sense event signals may provoke state transitions which typically reset escape intervals. In general when escape interval times expire, a pace event signal is generated which is communicated to one of the pulse generators. This will provoke the generation of and delivery of a stimulating pulse to the heart. The various values for the escape intervals are referred to as therapy parameters. It is understood that these therapy parameters can also alter the effective modality of the pacemaker. Consequently, sensor variance based changes to the pacemaker may alter either the therapy delivered to the patient or the operation of the pacemaker itself. Alternate therapy can be provided by a defibrillation generator 23 switched on the lead system with a set of switches 19.

A physiologic sensor, such as an activity sensor 16, is coupled to the pacemaker processor 26 to provide information about the physical activity and metabolic state of the patient. It is also possible to use two sensors. For this reason, a partial pressure of oxygen sensor illustrated in FIG. 1 as 25. In operation, either sensor or both sensors can be interrogated to control the function of the device.

The pacemaker illustrated includes memory to store various operating parameters. Several memory locations are shown associated with the pacemaker processor 26. For example, the attending physician may prescribe a mode and lower escape rate stored at locations 31 and 32 respectively. Other memory locations are shown in FIG. 1 and they are discussed with respect to the vasovagal detection methodology.

The illustrative activity sensor 16 is of conventional design and is coupled to conventional analog signal conditioning circuits which convert the motion of the patient into a digital activity signal which may be collected in a counter. The current value of this counter may be called Act_Val and it may be stored in memory location 54. Over time, a representative value of the patient activity may be formed from a sequence of Act_Val values and called Act_Avg. In this illustrative version of the invention, a running average is formed and this value may be stored in memory location 55. This technique should work for any sensor which detects a physiologic variable and generates a sequence of measured sensor values. It may be noted that some types of activity sensors use a cantilever beam structure which gives different sensor outputs depending on patient position. This form of sensor can distinguish a patient that is erect from one that is supine. Such sensors may provide additional sensitivity and specificity for vasovagal syncope applications. The minimum requirement for a sensor and the signal processing processes is that the sensor distinguish at least two different metabolic states. It is also useful to compute and store a measure of the variability of the activity signal. Location 56 may be devoted to storage of an activity variance value called Act_Var. Thus the activity channel provides information about patient activity level on a relatively current as well a historic basis.

FIG. 2 shows illustrative values for these data in a graphical format. Typically, the counter will accumulate activity "counts" over a specified time interval. Usually, this counting process will be synchronized with the heart beat and occur about once a second, although this value is representative and not critical. Consequently, the counter value corresponds to a current value for a measured patient activity value. The bars in the figure illustrate the value of the activity counter at the time periods shown in the figure. For example, bar 60 shows the Act_Val count for t=3. The sequence of values shown by the bars may be averaged in many ways. For illustration, a running average value for the Act_Val is represented by the dotted line 62 and is called "Activity Average" (Act_Avg). Other effective approaches to averaging include adding 1/32 of the current value of Act_Val to $^{31}/_{32}$ of the historical value of Act_Avg. This approach acts as a low pass filter which prevents rapid changes in the value of Act_Avg which is a benefit when the value of Act_Avg is used to modulate the pacemaker escape interval. It should be noted that Act_Val represented by bar 60 is above the then current Act_Avg value. Similarly the bar 64 represents a value of the Act_Val which is below the running average over the same time interval. It is useful to track the variability of the Act_Val measurements and to collect them in a histogram. To measure the variance of the patient activity, the value of Act_Val at time t=3 (bar 60) can be subtracted from the value of Act_Val at a later time such as t=5 (bar 64). The difference between the current value of activity variance and a more remote value is shown graphically by line 63. The square root of the square of this difference (delta Act_Val) is of the most interest. This process gives the standard deviation of the Act_Val values and ignores the sign of the changes. The process of comparing the values of Act_Val from different times allows the measurement to sensitively reflect changes in the patient's metabolic state. For example, a normally active and ambulatory patient would be likely to have a great difference between Act_Val measures if taken a second or so apart. By contrast, the same patient sleeping would be expected to have values of Act_Val which are very close in value even when measured several seconds apart since the level of physical activity during sleep is low. Consequently, it is the magnitude of the variance and not the sign which is significant for the present process. If a relatively large amount of data is collected over a time period which includes a period of sleep, one can construct a normalized histogram of activity variance as presented in FIG. 3.

FIG. 3 is a histogram that shows activity variance data collected over a day or more. When the patient is awake and nominally active, the values of Act_Var vary widely. These large variance values are shown on the right side of the histogram and are labeled 66. Activity variance values in this region are regarded as indicative of a patient who is awake and at rest. During sleep, the level of activity falls and, more importantly, the variance between sequential activity measurements are small and Act_Var tends toward zero. Therefore the left side of the histogram is dominated by events which occur during sleep. Numeral 68 identifies this portion of the histogram. When treated in this way, the there is a distinct boundary between activity variance values associated with sleep and those that result from normal physical activity. The activity variance threshold (Act_Var_Thsld) represents the boundary between this bimodal distribution. In practice, the pacemaker can automatically find and set this threshold value. It could also be remotely programmed by a physician if desired. Depending upon how the Act_Var measure is computed, this parameter can have a long or short time constant. For the treatment of vasovagal syncope, it is best to have a relatively long time constant of several minutes or more. This can be effectively achieved by adding $^{1}/_{32}$ of the current measure of Act_Var to $^{31}/_{32}$ of the existing value of the Act_Var measure. An important feature of this methodology is that the sensor values are partitioned in the measurement space into two distinct subsets of data. Each subset represents a distinct metabolic state for the patient. In the case of activity, the bimodal distribution corresponds to a value indicative of an inactive patient or an awake and normally active patient.

The derivation of a sensor measurement which reliably distinguishes two or more metabolic states of the patient having a relatively long time constant permits the use of the measurement to detect precipitous changes in the metabolic state of the patient. In general, the invention includes means for computing the variance of a sequence of sensor values. Next, a set of sensor variance values is generated. This set is partitioned into a subset of sensor variance values indicating normal active metabolic demand and a subset indicating lower metabolic demand. Thus, the set of activity measurements is separated into two subsets indicating different metabolic states. The ability to distinguish between two metabolic states permits the pacemaker to alter its operation based upon the state of the patient. It is likely that the best use of this ability will be to vary a pacing or therapy parameter. It is possible to invoke almost any change or algorithm within the device. In this way, the invention may be considered a trigger for other algorithmic behavior in the device. This sensor variance methodology is appropriate for many sensors although it is easiest to describe with respect to patient activity. It should also be noted that the metabolic state of the patient may be divided into more than two states. The threshold value shown by line 67 is an alternate threshold that may be used with activity to define three separate metabolic states.

Figure 4:
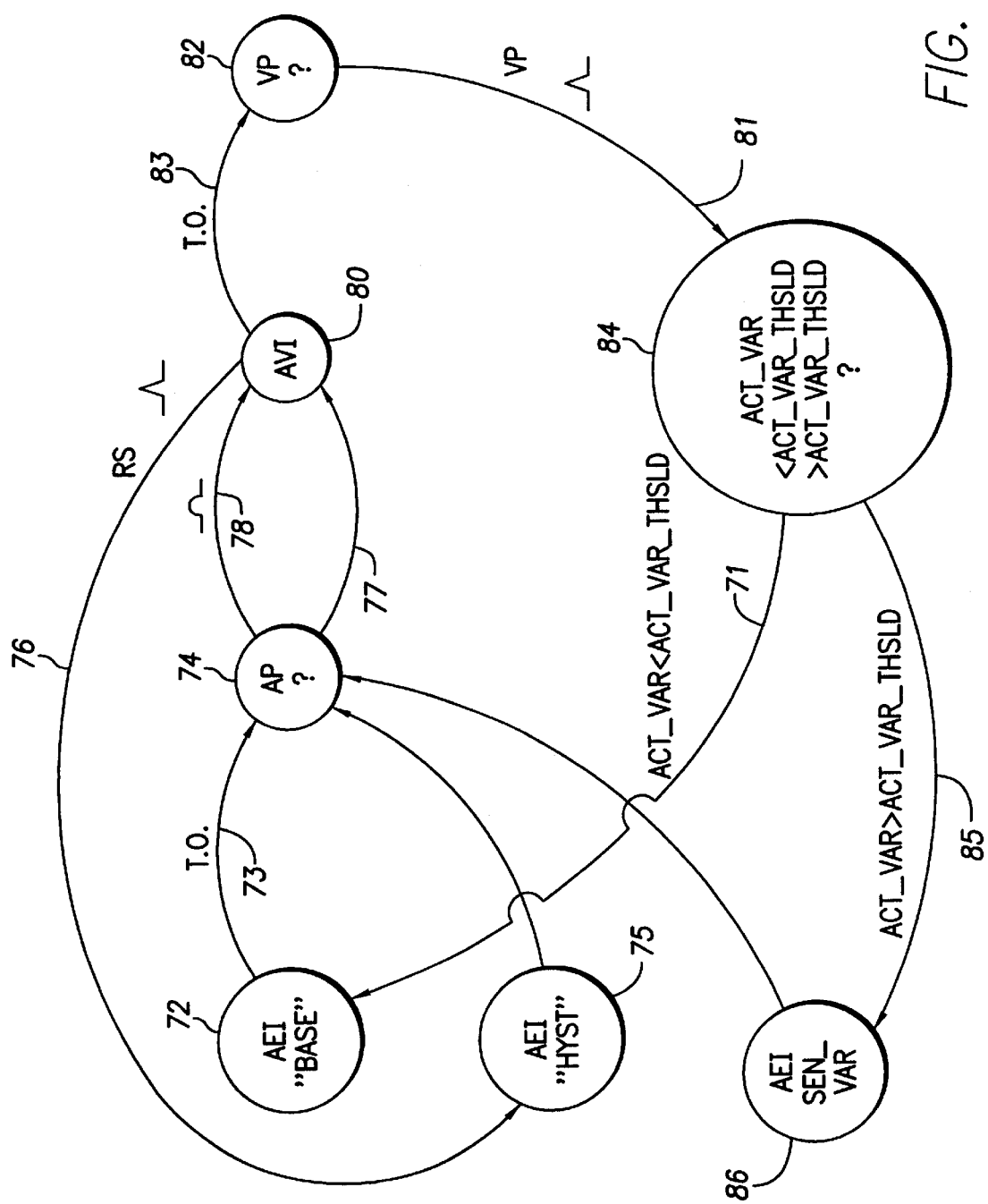
FIG. 4 is a state diagram of a dual-chamber pacemaker incorporating the invention.

FIG. 4 shows a state diagram of a DDI(R) pacemaker showing how the activity threshold data along with intrinsic heart rate data can be used in a DDI(R) pacemaker to accommodate a vasovagal patient. Certain refractory timers and noise sampling timers whose operation are well known in the art are not shown on the state diagram to improve the clarity of the figure. Beginning at state 72, the activity modulated base rate atrial escape interval (AEI) is timed out. The pacemaker leaves state 72 by state transition 73 which corresponds to the base atrial escape interval time out. Next, the pacemaker enters the atrial pacing state 74 where the decision to pace the atrium is made. If an atrial sense event (PS) has been detected then the pacemaker does not pace the atrium and the state transition 77 reflects this inhibited operation. If atrial pacing is required, then the pacemaker leaves state 74 by state transition 78 which corresponds to the delivery of an atrial pace event (AP). Either transition takes the pacemaker to the atrial-ventricular delay interval state 80 (AVI) where the A-V delay is timed. If the state timer for AVI state 80 times out, then the pacemaker moves to the ventricular pacing state 82 where a ventricular pace event (VP)is generated. After a ventricular pace event occurs, the pacemaker moves to the activity monitoring state 84 by transition 81. In state 84, the current value of the sensor variance Act_Var is compared to the threshold value Act_Var_Thsld. If the current activity variance exceeds the threshold value, then the assumption is that the patient has recently been awake and physically active. In this case the state transition 85 moves the pacemaker to set the atrial escape interval to a sensor variance escape interval timing in state 86. If the value of the Act_Var is below the threshold value, then the patient may be sleeping and no intervention at a high rate is needed. In this instance the pacemaker moves to state 72 through transition 71 where the atrial escape interval is set to a base rate. The hysteresis operation occurs if a ventricular sense event occurs during the atrial-ventricular timing state 80. A detected R-wave (RS) provokes a transition to the hysteresis escape interval state 75. This is shown in the figure as state transition 76. In state 75, the typically longer hysteresis interval is timed out. A patient in normal sinus rhythm with intact conduction would interact with the pacemaker through the states and state transitions shown with a bold line in FIG. 4.

As described above, the pacemaker carries out a method where the patient's heart rate is continually monitored. In this fashion the sense amplifiers and escape timers form a means for detecting asystole. If the patient is experiencing asytole then the device delivers a pacing stimulus and interrogates the state of the patient's activity variance. If the variance measure indicates that the patient has recently been active, then the device selects a sensor variance escape interval which is likely to be short (high rate) for a vasovagal patient. It should be noted that the sensor variance rate is independent of the "base" rate and could be a lower rate than the base rate. In this exemplary pacemaker, the device remains in DDI(R) mode.

FIG. 5 shows an atrial synchronized DDD pacemaker which incorporates the invention. This pacemaker lacks sensor based rate modulation and also lacks the hysteresis function. This embodiment illustrates the use of sensor variance to alter one type of therapy parameter. In this pacemaker, the base escape interval is timed out in V-A timer state 100. If the timer times out, then transition 102 takes the device to the atrial pacing state 104. Transition 106 corresponds to the delivery of an atrial pace event and moves the device into the activity variance monitoring state 114. In this sensor variance monitoring state, the device compares the current value of the Act_Var value with the threshold value Act_Var_Thsld. If the patients current activity variance indicates recent activity (Act_Var>Act_Var_Thsld), then the device enters an A-V delay escape interval state 108 where a relatively short A-V delay is timed out. If the value of Act_Var is less than he threshold value, than the device enters state 110 where a slightly longer A-V delay may be timed out. Either of the sensor variance selected escape intervals will result in a transition into the ventricular pacing state 112, if no ventricular sense events occur. In the ventricular pacing state 112 the device generates a pacing stimulus through the ventricular pulse generator 18. The delivery of the pacing stimulus corresponds to the state transition 120 which returns the devices to the V-A timing state 100. Ventricular sense events occurring during the A-V delay interval also inhibit the delivery of a pacing stimulus and return the device to the V-A timing state through either state transition 124 or state transition 120. In this pacemaker, the transition into a sensor variance A-V delay shows how the invention can trigger another algorithm based upon sensor variance. In the DDD mode of operation, the use of the hysteresis function is based essentially on the current atrial rate. Furthermore, AV delay change or modulation is a secondary function.

Figure 6:
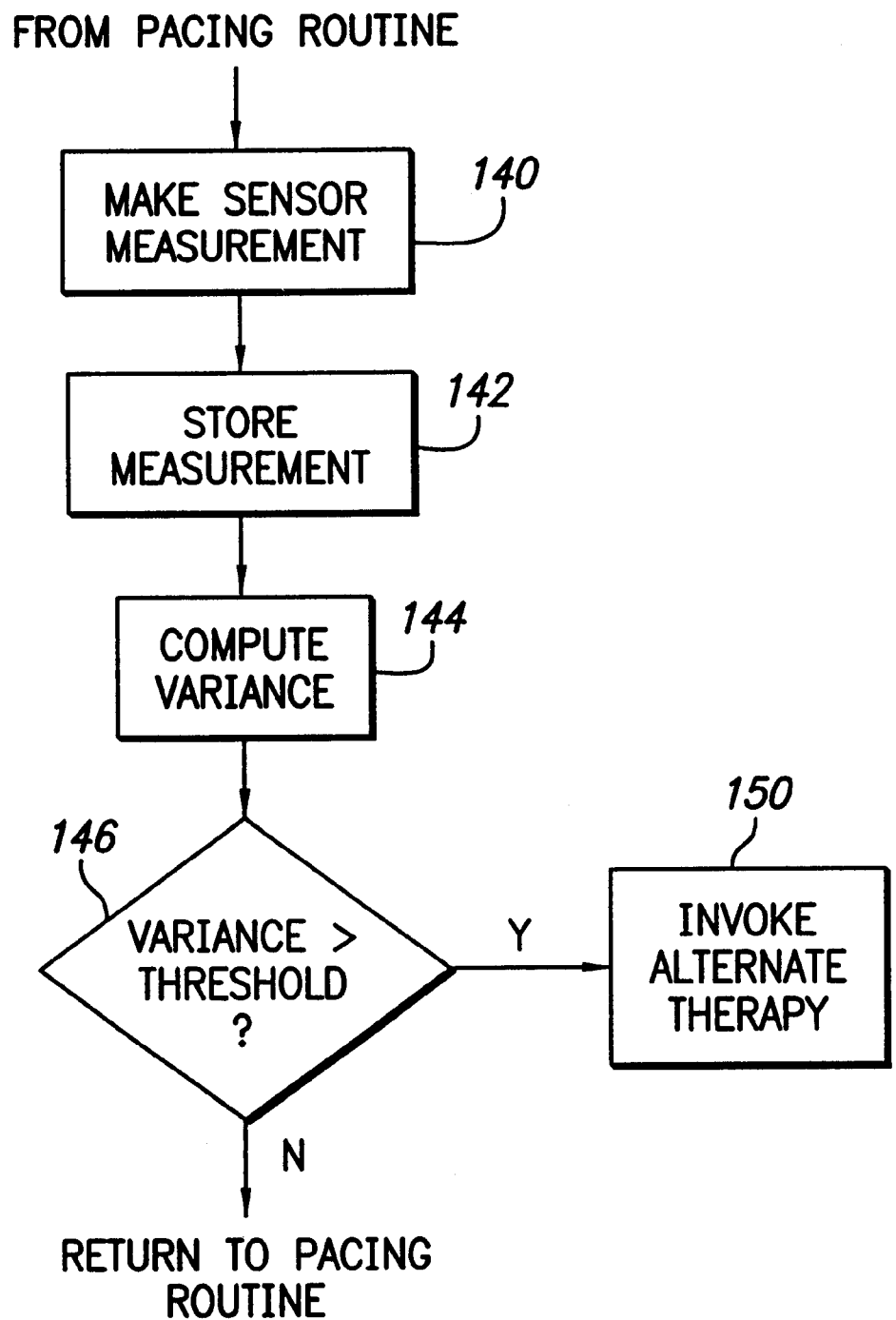
FIG. 6 is a flowchart showing one embodiment of the sensor variance process.

FIG. 6 is a flowchart showing an implementation of sensor variance controlled device where therapy is directed by a sensed change in sensor variance. For example block 140 can be entered from a pacing routine. In block 140, a sensor measurement is made and stored in memory as seen in connection with block 142. In block 144, the sensor variance is computed. In block 146, the sensor variance value is compared with a preset threshold. If the value exceeds a level depicted by a threshold 67, as seen in FIG. 3, then the decision block 146 will direct program flow to block 150 where an alternate therapy may be delivered. If the sensor variance is below the threshold then the program returns to the normal pacing routine.

What is claimed is:

1. An implantable medical device for stimulating a patient's heart through at least one electrode implanted in electrical contact with the patient's heart, the medical device comprising:

a pulse generator electrically coupled to the electrode and configured to generate stimulation pulses to thereby stimulate the patient's heart at a controlled rate;

a detection circuit electrically coupled to the electrode and configured to receive signals from the patient's heart indicating intrinsic heart beats;

a sensor circuit for monitoring a physiologic variable of the patient and for determining whether the patient is in one of at least two physiologic states, wherein a first physiologic state corresponds to the patient being inactive and a second physiologic state corresponds to the patient being active; and a processor, coupled to the pulse generator, the detection circuit, and the sensor circuit, for increasing the controlled rate in response to the absence of an intrinsic heart beat when the sensor circuit determines that the patient is in the active physiologic state.

2. The medical device of claim 1 wherein the sensor circuit measures the activity level of the patient.

3. The medical device of claim 1 wherein:

the sensor circuit periodically measures a physiologic value and periodically determines the difference between sequential physiologic values to generate a sensor variance signal; and wherein the sensor circuit determines the physiologic state of the patient according to the sensor variance signal.

4. The medical device of claim 3 wherein the physiologic states are determined according to at least one threshold value which divides the sensor variance signal values into at least two sets of values corresponding to physiologic states.

5. The medical device of claim 1 wherein the sensor circuit measures the body position of the patient.

6. The medical device of claim 1 wherein the sensor circuit measure the oxygen content of the patient's blood.

7. The medical device of claim 1 wherein the controlled stimulation rate is determined according to an escape interval and the controlled stimulation rate is increased by decreasing the escape interval.

8. A method for detecting vasovagal syncope and providing treatment to a patient's heart by applying stimulation pulses at a controlled stimulation rate through at least one electrode implanted in electrical contact with the patient's heart, the method comprising:

monitoring a physiologic sensor to determine a current physiologic value;

determining a sensor variance signal in response to the difference between consecutively monitored physiologic values;

determining a physiologic mode in response to the variance signal, wherein the physiologic mode includes indicating that that the patient is in an inactive or an active state;

monitoring for intrinsic heart beats; and increasing the controlled stimulation rate in response to the absence of an intrinsic heart beat when the physiologic mode indicates the patient being in an active state and thereby treating vasovagal syncope.

9. The method of claim 8 wherein the determining the physiologic mode is determined according to a threshold value which divides the sensor variance signal values into at least two sets of values corresponding to physiologic states.

10. The method of claim 8 wherein the physiologic sensor measures the activity level of the patient to determine the physiologic mode.

11. The method of claim 8 wherein the physiologic sensor measures the oxygen content of the patient's blood to determine the physiologic mode.

12. The method of claim 8 wherein the physiologic sensor measures the patient's body position to determine the physiologic mode.

13. The method of claim 8 wherein the controlled stimulation rate is determined according to an escape interval and the controlled stimulation rate is increased by decreasing the escape interval.

\* \* \* \* \*